*(12)* United States Patent
Horikoshi et al.

(10) Patent No.: US 9,703,188 B2
(45) Date of Patent: Jul. 11, 2017

(54) AGGLUTINAT FOR PELLICLE, A PELLICLE USING IT AND A METHOD FOR EVALUATING PELLICLE

(71) Applicant: SHIN-ETSU CHEMICAL CO., LTD., Tokyo (JP)

(72) Inventors: Jun Horikoshi, Annaka (JP); Yu Yanase, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 135 days.

(21) Appl. No.: 14/931,267

(22) Filed: Nov. 3, 2015

(65) Prior Publication Data

US 2016/0187771 A1  Jun. 30, 2016

(30) Foreign Application Priority Data

Dec. 25, 2014  (JP) ................................. 2014-261591

(51) Int. Cl.
*G03F 1/64* (2012.01)
*G01N 21/70* (2006.01)
*C09K 11/77* (2006.01)

(52) U.S. Cl.
CPC ............ *G03F 1/64* (2013.01); *C09K 11/7734* (2013.01); *G01N 21/70* (2013.01)

(58) Field of Classification Search
CPC ........ G03F 1/64; C09K 11/7734; G01N 21/70
USPC ......................................... 430/5; 23/305 RE
See application file for complete search history.

(56) References Cited

U.S. PATENT DOCUMENTS

| | | |
|---|---|---|
| 4,861,402 A | 8/1989 | Gordon |
| 2009/0286169 A1 | 11/2009 | Shirasaki |
| 2015/0286134 A1 | 10/2015 | Horikoshi |
| 2016/0187771 A1 | 6/2016 | Horikoshi et al. |

FOREIGN PATENT DOCUMENTS

| | | |
|---|---|---|
| EP | 2120093 A1 | 11/2009 |
| EP | 2927745 A2 | 10/2015 |
| EP | 3037879 A1 | 6/2016 |
| JP | S58-219023 A | 12/1983 |
| JP | S63-27707 A | 2/1988 |
| WO | 2007/023869 A1 | 3/2007 |

OTHER PUBLICATIONS

Europe Patent Office, "Search Report for European Patent Application No. 15003172.2," May 2, 2016.
Li, C. et al., "Full-field measurement of dynamic stress by mechanoluminescence sensing film," Second International Conference on Smart Materials and Nanotechnology in Engineering, Proceedings of SPIE, Jul. 25, 2009, p. 749335-749335-7, vol. 7493, USA.
Xu, C. et al, "Dynamic visualization of stress distribution by mechanoluminescence image," Applied Physics Letters, Jan. 10, 2000, p. 179-181, vol. 76, No. 2, American Institute of Physics, USA.

*Primary Examiner* — Christopher Young
(74) *Attorney, Agent, or Firm* — Manabu Kanesaka

(57) ABSTRACT

A pellicle is proposed in which the agglutinant layer which enable the pellicle to be adhered to a photomask is doped with a mechanoluminescent material so that the uniformness of the thickness of the agglutinant layer can be confirmed, when the pellicle is adhered to the photomask, by observing visually or by CCD camera for any irregularity in the pattern of the light emitted from the agglutinant layer.

13 Claims, 1 Drawing Sheet

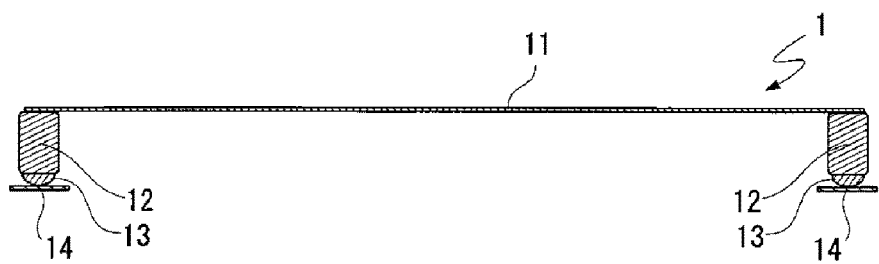

AGGLUTINAT FOR PELLICLE, A PELLICLE USING IT AND A METHOD FOR EVALUATING PELLICLE

The present non-provisional patent application claims priority, as per Paris Convention, from Japanese Patent Application No. 2014-261591 filed on Dec. 25, 2014, the disclosure of which is incorporated by reference herein in its entirety.

FIELD OF THE INVENTION

The present invention relates to a pellicle for lithography, useful as a dust-fender employed in the scenes of manufacturing semiconductor devices, printed circuit boards, liquid crystal display panels, etc.; and in particular the invention relates to an agglutinant for pellicle, a pellicle using it, and a method for evaluating a pellicle.

BACKGROUND TECHNOLOGY

In manufacturing semiconductor devices such as LSI and super-LSI or in manufacturing a liquid crystal display panel or the like, a circuit pattern is made by irradiating a light to a semiconductor wafer or a negative plate for liquid crystal, but problems occur if a dust particle is sticking to a photographic mask or a reticle (hereinafter these are referred to as "photomask") used in this stage; for then the pattern's edges become blurred and what is more the under base gets smeared in black, whereby the dimension, quality, appearance, and other aspects of the resulting product are degraded.

Thus, these works are usually performed in a clean room, but, even in a clean room, it is yet difficult to keep the photomask clean all the time. Hence, the exposure light irradiation is conducted only after a pattern-including part of the surface of the photomask is sheltered by a pellicle as a dust fender. Under such circumstances, foreign particles do not directly adhere to the surface of the photomask, but only onto the pellicle membrane, and thus by setting a photo focus at a pattern on the photomask at the time of lithographing, the foreign particles on the pellicle membrane do not affect the transferred image.

In general, a pellicle is made in a manner such that a transparent pellicle membrane made of cellulose nitrate, cellulose acetate, a fluorine-containing polymer or the like, which transmit light well, is adhered to an upper annular face of a pellicle frame, which is made of an aluminum alloy, a stainless steel, polyethylene or the like, after applying to the upper annular face a solvent which dissolves the pellicle membrane well, and then by drying the solvent by blown air (ref. IP Publication 1), or after applying to the upper annular face an adhesive made of a material such as an acrylic resin or an epoxy resin (ref. IP Publications 2, 3). Further, on a lower annular face of the pellicle frame is laid an agglutinant layer made of a polybutene resin, a polyvinyl acetate resin, an acrylic resin, a silicone resin or the like for attaching the pellicle frame to the photomask, and over this agglutinant layer is laid a releasable liner (separator) for protecting the agglutinant layer.

PRIOR ART PUBLICATIONS

[IP Publications]
[IP Publication 1]
Japanese Patent Application Publication S58-219023 (1983)
[IP Publication 2]
U.S. Pat. No. 4,861,402
[IP Publication 3]
Japanese Publication for Public Review of Allowable Patent Application S63-27707 (1988)

SUMMARY OF THE INVENTION

Problems the Invention Seeks to Solve

A pellicle is adhered to a photomask by means of its agglutinant layer in order to prevent foreign particles from sticking to a pattern on the photomask; if the agglutinant layer is not formed evenly and without local ups and downs and heaving all around the pellicle frame face and if the pellicle is not adhered to the photomask precisely uniformly, such unevenness or ups and downs and heaving of the agglutinant layer face would give rise to an uneven stress distribution at the interface between the photomask and the pellicle with a possible result that the pattern on the photomask is deformed.

In recent years, in order to prevent the pattern on the photomask from deforming as the pellicle is adhered to the photomask, a pellicle frame with improved flatness is used or the agglutinant is applied with higher precision to obtain an agglutinant layer with improved surface flatness; however, if there are even small ups and downs or heaving in the surface of the agglutinant layer or an unevenness in the width of the agglutinant layer, or a slight angle between the pellicle and the photomask, then at the time of pellicle adhesion to the photomask, the pattern on the photomask undergoes a deformation.

There are several methods for applying the agglutinant to the pellicle frame without giving it ups and downs or heaving, but there has not been a method specialized for evaluating with precision the shapes and conditions of the agglutinant layer formed after the application; there is only a simplified method in which a pellicle is adhered to a glass base plate and the quality of the adhesion of the agglutinant layer is observed from the backside of the glass base plate visually or by a CCD camera. However, although this method can evaluate the uniformity of the width of the agglutinant layer as it is applied, it cannot inspect how much ups and downs or heaving have (had) occurred.

If it is desired, in the past, to evaluate more precisely the shape of the agglutinant layer, it was necessary to make measurements, after adhering the pellicle to a glass base plate, by means of an apparatus such as FlatMaster and UltraFlat (both commercial products of SOL Co., Ltd.). However, the measurement depending on these apparatuses was complicated and time-consuming.

As such, there has been the problem of difficulty to evaluate with precision and simplicity the ups and downs and heaving of the agglutinant layer formed on the pellicle frame.

It is therefore an object of the present invention to solve the above-stated problems and in particular to provide an agglutinant for pellicle that enables simplified and high-precision evaluation of ups and downs and heaving formed to the agglutinant layer laid on the pellicle frame; the present invention also provides a pellicle using such an agglutinant and a method for evaluating the pellicle.

Means to Solve the Problem

In order to attain above-mentioned objects, the present inventors discovered that if an agglutinant layer formed on a pellicle frame had ups and downs or heaving, there occurs a stress difference between that portion of the agglutinant layer which has ups and downs or heaving and that portion of the agglutinant layer which is free of them, when the pellicle is adhered to the photomask; hence they theorized that if a material that emits light in response to a stress (mechanoluminescence) is ingrained in the agglutinant which forms the agglutinant layer, then it becomes possible to know the degree of the ups and downs or heaving of the agglutinant layer with ease and precision by observing the pattern of the light emission, because the amount of the light emission varies depending on the various stress differences caused by the ups and downs or heaving of the agglutinant layer as the pellicle is adhered to the photomask; as the result, the inventors possessed and completed the invention relating to an agglutinant for pellicle, a pellicle, and a method for evaluation of the pellicle.

Therefore, the agglutinant for pellicle according to the present invention is an agglutinant for pellicle which binds the pellicle to the photomask, and is characteristic in that it contains a light emitting material which emits light in response to stress (herein after, "mechanoluminescent material").

The agglutinant for pellicle according to the present invention contains a mechanoluminescent material, which emits a light whose amount of luminescence varies depending on the stress built in the agglutinant; when a pellicle with the agglutinant laid on one of its annular face is adhered to a photomask, and if on this occasion the thickness of the agglutinant layer formed of the agglutinant is not uniform and had a rise, then a greater stress is imposed on the risen portion of the agglutinant layer than on a flatter portion, so that the mechanoluminescent material contained in the agglutinant emits a stronger light. On the other hand, if there is a recess in the agglutinant layer formed of the agglutinant, then a smaller stress is imposed on the recessed portion of the agglutinant layer than on the surrounding portion, so that the mechanoluminescent material contained in the agglutinant emits a weaker or no light. By observing the pattern of the light emission, it is possible to evaluate the ups and downs and heaving of the agglutinant layer with ease and precision.

The mechanoluminescent material to be used can be any such material whose amount of luminescence varies depending on the stress, and an example is strontium aluminate-based material which is activated by containing europium (Eu) ion as the luminescent ion.

A dosage of the mechanoluminescent material is preferably 50 through 1,000 mass parts as opposed to 100 mass parts of agglutinant.

A main ingredient of the agglutinant is preferably a silicone composition or an acrylic composition.

A pellicle according to the present invention comprises a pellicle membrane, a pellicle frame on one annular face of which is adhered the pellicle membrane, and an agglutinant layer laid on the other annular face of the pellicle frame for enabling the pellicle to be adhered to a photomask; and the pellicle of the present invention is characteristic in that the agglutinant layer is made of the agglutinant for pellicle of the present invention.

A method for evaluating the pellicle according to the present invention comprises steps of adhering the pellicle of the present invention to a photomask and then observing a luminescent amount or strength of the agglutinant layer of the pellicle.

Effect of the Invention

According to the present invention, it is possible to evaluate the quality of the flatness of the agglutinant layer formed on the pellicle frame with ease and precision since it is possible to discover the presence of ups and downs and heaving of the agglutinant layer by visually inspecting the strength of the luminescence emitted from the agglutinant layer.

Furthermore, it is possible to measure the luminescence area and luminescence amount by means of CCD camera as well as an image processing equipment so that the degrees of the ups and downs and heaving in the agglutinant layer formed on the pellicle frame can be evaluated quantitatively. As a result, it is possible to conduct a highly accurate and reliable evaluation which is not affected by difference in inspectors' skills.

BRIEF DESCRIPTION OF DRAWINGS

FIG. 1 A schematic longitudinal sectional view showing an example of a pellicle of the present invention in which an agglutinant for pellicle of the present invention doped with a mechanoluminescent material is used.

EXAMPLES TO EMBODY THE INVENTION

Here the present invention is explained in greater detail with reference to the drawing, and one should not construe the invention to be limited to the example or the drawing.

FIG. 1 is a schematic longitudinal sectional view showing the example of the pellicle of the present invention in which the agglutinant for pellicle of the present invention doped with a mechanoluminescent material is used.

As shown in FIG. 1, a pellicle 1 embodying an example of the present invention is constructed in a manner such that a pellicle membrane 11 is adhered to an upper annular face of a pellicle frame 12, which has a shape corresponding to the shape of a photomask (glass base plate) to which the pellicle 1 is tensely adhered, generally the shape of the pellicle frame 12 being quadrilateral (either rectangular or square), and such that an agglutinant layer 13 is formed on a lower annular face of the pellicle frame 12 for the purpose of enabling the pellicle 1 to be adhered to the photomask (glass base plate). This agglutinant layer 13 is one that is doped with a mechanoluminescent material; in other words this agglutinant embodies the agglutinant according to the present invention. Also, a releasing layer (separator) 14 for protection of the agglutinant layer 13 is detachably adhered to the exposed face of the agglutinant layer 13.

It is noted that, in the present invention, there are no limitations to the materials of which the pellicle membrane or pellicle frame are made, and it is possible to use any conventionally known materials, but from the viewpoints of rigidity and the machinability, the pellicle frame is preferably made of metal. The pellicle membrane may be adhered to the pellicle frame in any known method.

In the pellicle of the present invention, the agglutinant of the present invention is laid on the lower annular face of the pellicle frame in a manner such that the resulting agglutinant layer has a predetermined width (normally equal to or smaller than the width of the frame bar) and such that it enables the entirety of the lower annular face of the pellicle frame to be adhered to a photomask (glass base plate).

As is explained above, the agglutinant for pellicle of the present invention is doped with a mechanoluminescent material, but the base agglutinant can be selected from known agglutinants. Especially silicone agglutinant consisting mainly of silicone composition and acrylic agglutinant consisting mainly of acrylic composition are preferable.

Examples of the silicone agglutinant that can be used as the base agglutinant include X-40-3122, KR-3700, X-40-3103, and X-40-3264 (all commercial products of Shin-Etsu Chemical Co., Ltd.).

Examples of the acrylic agglutinant that can be used as the base agglutinant include SK-1425, SK-1495 and the like of SK Dyne series (all commercial products of Soken Chemical & Engineering Co., Ltd.).

Among the above-named silicone agglutinants, X-40-3122 (commercial product of Shin-Etsu Chemical Co., Ltd.) is preferable because it is high in adhesion strength and contains less low molecular weight siloxanes. Also, among the above-named acrylic agglutinants, KS-1495 (commercial product of Soken Chemical & Engineering Co., Ltd.) is preferable because it is high in adhesion strength and operability.

The mechanoluminescent material with which the agglutinant for pellicle of the present invention is doped is not limited so long as it emits light in response to stress; but a preferred material is a strontium aluminate which is activated by containing europium (Eu) ion or an europium compound as the source of europium ion. Strontium aluminate is a compound represented by a formula:

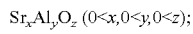

$Sr_xAl_yO_z$ (0<x, 0<y, 0<z);

and examples of this include $SrAl_2O_4$, $SrAl_4O_7$, $Sr_4Al_{14}O_{25}$, $SrAl_{12}O_{19}$, and $Sr_3Al_2O_6$. Strontium aluminate can be obtained through a reaction between alumina and strontium.

Examples of alumina include α alumina, θ alumina, κ alumina, δ alumina, η alumina, χ alumina, γ alumina, and ρ alumina. Among these, α alumina, θ alumina and η alumina are preferable to use.

Choice for the strontium compound is not specially limited, and its examples include strontium carbonate, strontium oxide, strontium hydroxide, strontium halide, strontium sulphate, strontium nitrate, and strontium hydrogen phosphate.

The europium compound is not limited either, and it can be europium carbonate, europium oxide, europium chloride, europium sulphate, europium nitrate, or europium acetate.

The method for making the mechanoluminescent material is not specially limited; an example is to first cause an alumina to react with a strontium compound to thereby obtain strontium aluminate, which is then added, together with a europium compound, to water and/or organic solvent where they are mixed together, and then to remove the water and/or the organic solvent, and to bake and pulverize the remnant solid matter into power or the like.

When a stress is imparted to this mechanoluminescent material, the part of it where the stress is imparted emits green light with a strength commensurate with the magnitude of the stress. The higher the concentration (dosage rate) of the mechanoluminescent material in the agglutinant is, the higher the agglutinant's light emission responsive becomes, but if the dosage of the mechanoluminescent material exceeds 1,000 mass parts against 100 mass parts of the base agglutinant, which is a raw material for the agglutinant for pellicle of the present invention, it becomes impossible to knead the mechanoluminescent material into the base agglutinant; on the other hand, if the said dosage is less than 50 mass parts, the light emission responsive to the stress becomes too weak to enable observation of the emitted light amount. Therefore, the dosage of the mechanoluminescent material is preferably 50 through 1,000 mass parts against 100 mass parts of the base agglutinant.

Also, it is acceptable to add different additives to the agglutinant for pellicle of the present invention, for different purposes, to extents that would not thwart the effects of the present invention. Examples of such additives include parting agent, pigment, dye, plasticizer, flame retardant, heat resistance improver, weather resistance improver, thixotropy imparting agent, antibacterial agent, and anti-mold agent.

Most of the above-mentioned mechanoluminescent materials are in powder form so that on occasions it is difficult to dispense the material uniformly in the base agglutinant. On such occasions, it is possible to disperse the mechanoluminescent material in a solvent and then add the solution to the base agglutinant; the possible solvents are such as an aromatic solvent like toluene and xylene, or an aliphatic solvent such as hexane, octane, isooctane, and isoparaffin, or a ketones solvent such as methyl ethyl ketone and methyl isobutyl ketone, or an ester solvent such as ethyl acetate and butyl acetate, or ethers solvent such as diisopropyl ether and 1,4-dioxane, or a mixture of any of these.

The application of the agglutinant for pellicle to the pellicle frame 12 is done by first diluting the agglutinant in a solvent, if necessary, and then laying the solution onto the lower annular face of the pellicle frame 12. Then by drying the agglutinant with heat and curing it, an agglutinant layer 13 is completed. The method for applying the agglutinant for pellicle can be brush painting, spraying, automatic dispensing, and the like.

The releasing layer (separator) 14 is for the protection of the agglutinant layer 13 until the pellicle is adhered to the photomask, and hence it is removed before the pellicle is used. For this reason, the releasing layer (separator) is used only in the case where the agglutinant layer is not protected by anything else during the time until the pellicle is adhered to the photomask. The product pellicle is distributed in the market generally in the form in which the releasing layer (separator) is attached to the agglutinant layer. Choice of the material for the releasing layer (separator) 14 is not limited, and can be made from anything known as a separator. Also, the releasing layer (separator) can be adhered to the agglutinant layer by any known tape adhesion method.

The pellicle having the agglutinant layer for pellicle of the present invention not only works as a regular dust-fender for the photomask, but also allows a simple and effective detection of the ups and downs and heaving of the agglutinant layer since it is possible to observe, from the backside of the glass plate photomask, the pattern of stress-responsive light emission from the agglutinant layer, after the pellicle is adhered to the photomask.

According to the evaluation method of the present invention, it is possible to observe visually the presence and strength of the light emitted from the agglutinant layer, so that the evaluation of the ups and downs and heaving of the agglutinant layer has become simpler and more accurate compared to the conventional pellicle which uses an agglutinant which does not contain mechanoluminescent material.

Furthermore, since it is possible to measure the luminescence area and luminescence amount by means of CCD camera and an image processing equipment, the degrees of the ups and downs and heaving of the agglutinant layer can be evaluated quantitatively; as a result, it is possible to set a clear evaluation standard for the agglutinant layer formed on the pellicle, and also a highly accurate and reliable evaluation which is not affected by difference in inspectors' skills is attained

EXAMPLES

Herein-below, the present invention will be explained in detail with reference to examples; however the scope of the present invention is not limited by the examples.

Example 1

Firstly, a pellicle frame made of an aluminum alloy [external size: 149 mm (long side); 122 mm (short side); 5.8 mm (height); 2 mm (bar width)] was brought in a cleanroom, and after being thoroughly washed with a neutral detergent and pure water, it was dried.

Meanwhile, an agglutinant for pellicle was prepared by mixing 100 mass parts of silicone agglutinant X-40-3122 (a commercial product of Shin-Etsu Chemical Co., Ltd.) with 100 mass parts of a mechanoluminescent material ML-032 (a commercial product of Sakai Chemical Industry Co., Ltd.), which is a strontium aluminate-based material activated by its content of europium (Eu) ion as the luminescent ion. Then the thus prepared agglutinant was applied to the lower annular face of the pellicle frame using an automatic dispenser (manufactured by Iwashita Engineering Co., Ltd.).

Next, the agglutinant was dried by air until it lost fluidity and then the pellicle frame was heated to 130 degrees C. whereby the agglutinant was cured and formed an agglutinant layer.

A pellicle membrane was adhered to the upper annular face of the pellicle frame via an adhesive named CYTOP CTX-A (a commercial product of ASAHI GLASS CO., LTD.), and excessive part of the pellicle membrane extending beyond the pellicle frame was trimmed off with a knife cutter, whereby a pellicle was completed.

Example 2

A pellicle was manufactured in the same manner as in Example 1 except that the agglutinant was prepared by mixing 100 mass parts of acrylic agglutinant SK-1495 (a commercial product of Soken Chemical & Engineering Co., Ltd.) with 100 mass parts of a mechanoluminescent material ML-032 (a commercial product of Sakai Chemical Industry Co., Ltd.).

Comparative Example 1

A pellicle was manufactured in the same manner as in Example 1 except that the agglutinant used was X-40-3122 (a commercial product of Shin-Etsu Chemical Co., Ltd.) but no mechanoluminescent material was added to it.

Comparative Example 2

A pellicle was manufactured in the same manner as in Example 1 except that the agglutinant used was SK-1495 (a commercial product of Soken Chemical & Engineering Co., Ltd.) and no mechanoluminescent material was added to it.

[Observation of Adhesion Quality of Agglutinant Layer]

The pellicles as obtained in Examples 1, 2 and Comparative Examples 1, 2 were respectively adhered to that face of a glass plate in which a lithography pattern was formed, and their agglutinant layers were inspected for their quality of adhesion visually as well as using a CCD camera in the following manners (Observations 1, 2).

1. Visual observation of the quality of adhesion under a fluorescent lamp:
   In a cleanroom under a fluorescent lamp, that face of the agglutinant layer by which the adhesion was effected was observed visually from the back side of the glass plate to which the pellicle was adhered; in particular the presence or non-presence of the emitted light and the strength of the emission were confirmed.
2. Observation of the quality of adhesion by CCD camera:
   Under the same conditions as above, that face of the agglutinant layer by which the adhesion was effected was observed from the back side of the glass plate to which the pellicle was adhered by means of a combination of a CCD camera and an image processing equipment (IV series, CV-X100 series; both commercial products of Keyence Corp.); in particular the presence or non-presence of the emitted light and the strength of the emission were confirmed.

It is noted that in the above Observations 1 and 2, in order to create a situation where the quality of the adhesion of the agglutinant layer to the glass plate is bad as well as a situation where said quality is good, the manner of adhering the agglutinant layer was intentionally controlled. Therefore, observation was conducted on both the situation where there were no ups and downs or heaving in the agglutinant layer (adhesion of high quality) and the situation where there were ups and downs or heaving (adhesion of poor quality), and the observation results were rated in the following standards. The rated results are shown in Table 1.

(Evaluation Standards)

Excellent: it was possible to evaluate quantitatively the ups and downs or heaving of the agglutinant layer under a predetermined condition.

Good: it was possible to visually detect the presence of the ups and downs or heaving of the agglutinant layer, so that evaluation of the quality of the adhesion is possible to a reasonable extent.

Bad: it was not possible to visually detect the presence of the ups and downs or heaving of the agglutinant layer, so that evaluation of the adhesion quality was not possible.

TABLE 1

|  |  | Example | | Comparative Example | |
|---|---|---|---|---|---|
|  |  | 1 | 2 | 1 | 2 |
| Visual Inspection | adhesion of high quality | Good | Good | Bad | Bad |
|  | adhesion of poor quality | Good | Good | Bad | Bad |
| by CCD camera | adhesion of high quality | Excellent | Excellent | Bad | Bad |
|  | adhesion of poor quality | Excellent | Excellent | Bad | Bad |

As can be seen from the results entered in Table 1, the agglutinant for pellicle of the present invention or the pellicle which uses it enables simple and accurate evaluation of the quality of the adhesion of the agglutinant layer, because, by linking the strength of the light emitted from the agglutinant layer to the magnitude of the stress that it has received at the time of the adhesion of the pellicle to the glass plate, it is possible to know the existence or non-existence of the ups and downs or heaving of the agglutinant layer.

REPRESENTATION OF REFERENCE NUMERALS

1: pellicle
11: pellicle membrane
12: pellicle frame

13: agglutinant layer (agglutinant containing mechanoluminescent material)
14: releasing layer (separator)

Scopes of what is claimed:

1. An agglutinant for pellicle for binding the pellicle to a photomask, characterized in that said agglutinant contains a mechanoluminescent material.

2. The agglutinant for pellicle as claimed in claim 1, wherein said mechanoluminescent material emits a light with a strength commensurate with a magnitude of a stress imparted to it.

3. The agglutinant for pellicle as claimed in claim 2 wherein said mechanoluminescent material is strontium aluminate-based material which is activated by containing europium (Eu) ion as a luminescent ion.

4. The agglutinant for pellicle as claimed in claim 1 wherein a main ingredient of said agglutinant is a silicone composition.

5. The agglutinant for pellicle as claimed in claim 1 wherein a main ingredient of said agglutinant is an acrylic composition.

6. The agglutinant for pellicle as claimed in claim 1 wherein a dosage of said mechanoluminescent material is 50 through 1,000 mass parts as opposed to 100 mass parts of said agglutinant.

7. A pellicle comprising a pellicle frame, a pellicle membrane which is tensely adhered to one annular face of said pellicle frame, and an agglutinant layer laid on another annular face of said pellicle frame for enabling said pellicle to be adhered to a photomask, wherein said agglutinant layer contains a mechanoluminescent material.

8. The pellicle as claimed in claim 7 wherein said mechanoluminescent material emits a light with a strength commensurate with a magnitude of a stress imparted to it.

9. The pellicle as claimed in claim 8 wherein said mechanoluminescent material is strontium aluminate-based material which is activated by containing europium (Eu) ion as a luminescent ion.

10. The pellicle as claimed in claim 7 wherein a main ingredient of said agglutinant layer is a silicone composition.

11. The pellicle as claimed in claim 7 wherein a main ingredient of said agglutinant layer is an acrylic composition.

12. The pellicle as claimed in claim 7 wherein a dosage of said mechanoluminescent material is 50 through 1,000 mass parts as opposed to 100 mass parts of said agglutinant.

13. A method for evaluating a pellicle characterized in that when said pellicle which contains a mechanoluminescent material in its agglutinant layer is adhered to a photomask via said agglutinant layer, a strength of light emitted from said agglutinant layer is inspected.

* * * * *